US005759780A

United States Patent [19]

Parker et al.

[11] Patent Number: 5,759,780
[45] Date of Patent: Jun. 2, 1998

[54] METHODS FOR ENRICHING TARGET NUCLEIC ACID SEQUENCES

[75] Inventors: Jay David Parker, Seattle; Kirsten Towne Smith, Newcastle; Peter Bruce Challoner, Seattle, all of Wash.

[73] Assignee: PathoGenesis Corporation, Seattle, Wash.

[21] Appl. No.: 626,166

[22] Filed: Mar. 29, 1996

[51] Int. Cl.$^6$ ............................... C12Q 1/68; C12P 19/34
[52] U.S. Cl. .................................................. 435/6; 435/91.2
[58] Field of Search .......................... 435/6, 91.2, 91.1

[56] References Cited

U.S. PATENT DOCUMENTS

| 5,132,207 | 7/1992 | Kohne et al. | 435/6 |
|---|---|---|---|
| 5,436,142 | 7/1995 | Wigler et al. | 435/91.2 |
| 5,501,964 | 3/1996 | Wigler et al. | 435/91.2 |

FOREIGN PATENT DOCUMENTS

| 2072231 | 12/1993 | Canada. |
| 0372524A2 | 6/1990 | European Pat. Off.. |

OTHER PUBLICATIONS

Shiloh, Y. et al., "Rapid cloning of multiple amplified nucleotide sequences from human neuroblastoma cell lines by phenol emulsion competitive DNA reassociation," *Gene*, 51:53–59 (1987).

Mor, O. et al., "Novel DNA sequences at chromosome 10q26 are amplified in human gastric carcinoma cell lines: molecular cloning by competitive DNA reassociation," *Nucleic Acids Res.*, 19(1):117–123 (1991).

Lisitsyn, N. et al., "Cloning the Differences Between Two Complex Genomes," *Science*, 259:946–951 (1993).

Lisitsyn et al., "Direct isolation of polymorpic markers linked to a trait b genetically directed representational difference analysis," *Nature Genetics*, 6:57–63 (1994).

Simons, J.N. et al., "Identification of two flavivirus-like genomes in the GB hepatitis agent," *Proc. Natl. Acad. Sci. USA*, 92:3401–3405 (1995).

Isuchiya, H. et al., "Isolation of Genes Differentially Expressed between the Yoshida Sarcoma and Long-survival Yoshida Sarcoma Variants: Orgin of Yoshida Sarcoma Revisted," *Jpn. J. Cance Res.*, 85:1099–1104 (1994).

Hubank, M. and Schatz, D.G., "Identifying differences in mRNA expression by representational difference analysis of cDNA," *Nucleic Acids Res.*, 22(25):5640–5648 (1994).

Muerhoff, A.S. et al., "Genomic Organization of GB Viruses A and B: Two New Members of the Flaviviridae Associated with GB Agent Hepatitis," *J. Virology*, 69(9):5621–5630 (1995).

Braun, B.S., "Identification of Target Genes for the Ewing's Sarcoma EWS/FLI Fusion Protein by Representational Difference Analysis," *Molecular and Cellular Biology*, 15(8):4623–4630 (1995).

Kohne, D.E. et al., "Room Temperature Method for increasing the Rate of DNA Reassociation by Many Thousandfold: The Phenol Emulsion Reassociation Iechnique," *Biochemistry*, 16(24):5329–5341 (1977).

Kunkel, L.M. et al., "Specific cloning of DNA fragments absent from the DNA of a male patient with an X chromosome deletion," *Proc. Natl. Acad. Sci. USA*, 82:4778–4782 (1985).

Nishi, Y. et al., "Characterization of N–myc amplification in a human neuroblastoma cell line by clones isolated following the phenol emulsion reassociation techique and by hexagonal field gel electrophoresis," *Mammalian Genome*, 2:11–20 (1992).

Zeng, J. et al., "Differential cDNA cloning by enzymatic degrading subtraction (EDS)," *Nucleic Acids Res.*, 22(21):4381–4385 (1994).

Miller R.D. and Riblet, "Improved phenol emilsion DNA reassociation technique (PERT) using thermal cycling," *Nucleic Acids Res.*, 23(12):2339–2340 (1995).

Schutte, M. et al., "Identification by representational difference analysis of a homozygous deletion in pancreatic carcinoma that lies within the BRCA2 Region," *Proc. Natl. Acad. Sci. USA*, 92:5950–5954 (1995).

Challoner, P.B. et al., "Plaque-associated expression of human herpesvirus 6 in multiple sclerosis," *Proc. Natl. Acad. Sci. USA*, 92:7440–7444 (1995).

Chang, Y. et al., "Identification of Herpesvirus-Like DNA Sequences in AIDS-Associated Kaposi's Sarcoma," *Science*, 266:1865–1869 (1994).

Drew, A.C. and Brindley, P.J., "Female-specific sequences isolated from *Schistosoma mansoni* by representational difference analysis," *Molecular and Biochemical Parasitology*, 71:173–181 (1995).

*Primary Examiner*—Eggerton A. Campbell
*Attorney, Agent, or Firm*—Christensen O'Connor Johnson & Kindness PLLC

[57] ABSTRACT

The invention includes selective amplification methods for enriching target nucleic acid sequences that are present in a first source of nucleic acid but absent from a second source of nucleic acid. These methods involve using phenol to enhance the rate of the hybridization step, as well as modifications for reducing the amounts of reagents required for the reactions. Also included are methods for identifying sequences shared by two or more populations of nucleic acids.

8 Claims, 3 Drawing Sheets

Fig. 1.

DIFFERENCE PRODUCT COMPARISON BY SUBTRACTION

FIRST RDA EXPERIMENTS:

FIRST COMPARISON SUBTRACTION:

SECOND COMPARISON SUBTRACTION:

Fig. 2.

DIFFERENCE PRODUCT COMPARISON: POOLING STRATEGY

DIFFERENCE PRODUCTS FROM FIRST RDA EXPERIMENTS:

DP(A)  DP(B)  DP(C)  DP(D)  DP(E)  DP(F)

FIRST COMPARISON SUBTRACTIONS:

SECOND COMPARISON SUBTRACTION:

METHODS FOR ENRICHING TARGET NUCLEIC ACID SEQUENCES

FIELD OF THE INVENTION

The subject invention relates to methods involving hybridization and polymerase chain reaction for selectively amplifying a target nucleic acid sequence that is present in one but absent from another population of nucleic acid sequences.

BACKGROUND OF THE INVENTION

Subtractive hybridization is a technique that has enabled investigators to detect nucleic acid sequences present in one but absent from another population of otherwise similar nucleic acid molecules. For the purposes of this technique, these populations are called tester and driver DNA, respectively. The basic rationale of subtractive hybridization is to introduce a physical difference between the driver and tester DNAs prior to allowing the two DNAs to hybridize. Based on this difference, hybrids derived solely from tester DNA are subsequently separated for further study. Thus, unwanted tester sequences are "subtracted" from the tester population.

The desired tester sequences (target sequences) are segregated from the unwanted tester sequences by the following strategy. During the hybridization step, driver DNA is provided in excess over the tester DNA so that most of the sequences common to tester and driver populations will form tester-driver duplexes. Hence, sequences common to both populations will segregate with the driver DNA when the physical difference is exploited after the hybridization step to separate the tester from the driver DNA. In the simplest form of subtractive hybridization, driver DNA is prepared for hybridization by methods that produce random ends (e.g., sonication or mechanical shearing), while tester is prepared by restriction endonuclease digestion that facilitates its later ligation into cloning vectors (e.g., Kunkel et al., *Proc. Natl. Acad. Sci. USA*, 82:4778–4782, 1985; Shiloh et al., *Gene*, 51:53–59, 1987; Mor et al., *Nucleic Acids Res.*, 19:117–123, 1991; Nishi et al., *Mammalian Genome*, 2:11–20, 1992).

A European patent application (EP 0372524 A2) discloses the use of a biotin label as the basis for separating tester-tester hybrids from driver-containing reassociation products. This method was used to isolate DNA corresponding to deletion mutations. Wild-type DNA used as tester was annealed with an excess of biotinylated deletion mutant DNA as driver, and the resulting biotin-containing duplexes were removed by binding to avidin coated beads. After several rounds of rehybridizing the unbound fraction with additional biotinylated driver, the recovered unbound duplexes were ligated to primers for polymerase chain reaction (PCR), amplified, and found to correspond to the sequences that had been deleted from the mutant DNA.

Lisitsyn et al., have proposed another way of combining subtractive hybridization and PCR in which PCR primers are ligated to the target DNA prior to its reassociation with driver DNA. (U.S. Pat. No. 5,436,142; Lisitsyn et al., *Science*, 259:947–950, 1993; Lisitsyn et al., *Nature Genetics*, 6:57–63, 1994). This method is called representational difference analysis (RDA), and does not require the use of any label such as biotin nor any post-reassociation physical separation techniques. RDA reportedly did not yield the desired target sequences unless the sequence complexity of the initial genomic DNA, i.e., the total number of unique sequences present, was first reduced before tester and driver were hybridized. To accomplish this complexity reduction, Lisitsyn et al. prepared "amplicons" from the initial DNA. In their method for making amplicons, both tester and driver DNAs are first cut with a restriction endonuclease that recognizes a six-base site. PCR adapters designed to reconstruct the original restriction site are ligated to the restriction fragments and then tester and driver DNAs are amplified separately by PCR. This procedure results in a population of relatively short fragments that represent substantially fewer sequences than were present in the initial DNA populations. Amplicon complexity typically represents between 1% and 12% of the starting material's complexity. After this amplification, the PCR primers are cleaved off both the tester and the driver DNAs, new and different adapters are ligated onto the tester DNAs, and an excess of driver amplicon is annealed with tester amplicon DNA. Hybridization products that form during this annealing step are PCR amplified. Tester-tester hybrids are amplified exponentially, but hybrids containing one strand from the tester and one strand from the driver will contain only one PCR primer and thus are amplified linearly rather than exponentially. Driver-driver hybrids cannot anneal with PCR primers and are not amplified at all. If greater enrichment of target sequences is desired, the adapters are cleaved off, and a different PCR adapter is ligated to the amplified material to avoid the accumulation of PCR products that might interfere with subsequent amplifications. The second adapter change is necessary to reestablish the 3' recessed ends to be filled in after the subsequent hybridization with driver DNA. Using RDA, Lisitsyn et al. could detect sequences present at a starting concentration of about one in $5 \times 10^6$, and also could detect genetic polymorphisms between individuals (Lisitsyn et al., 1994).

Other investigators have used RDA to detect differences in RNA transcripts by comparing cDNA populations transcribed from two different sources of RNA (Simons et al., *Proc. Natl. Acad. Sci. USA,*. 92:3401–3405, 1995; Hubank and Schatz, *Nucleic Acids Res.*, 22:5640–5648, 1994; Tsuchiya et al., *Jpn. J. Canc. Res.*, 85:1099–1104, 1994; Muerhoff et al., *J. Virology* 69:5621–5630, 1995; and Braun et al., *Mol. Cell. Biol.*, 15:4623–4630, 1995). As only a small percentage of genomic DNA gives rise to transcription products, mRNA populations are far less complex than genomic DNA. Hence, there is no need to reduce the complexity of cDNA populations prior to using them in subtractive hybridization. Accordingly, investigators applying RDA to the analysis of cDNA populations typically ligate the PCR adapters to restriction fragments produced by an enzyme that recognizes a 4-base site, e.g., Dpn II. Such fragments have an average length of 256 bases and are easily amplifiable by PCR.

Although RDA in its current form is very useful for analyzing cDNA populations, its sensitivity is not always adequate. For example, Braun et al. (1995) found that RDA apparently had not detected all of the expected target molecules and suggested that the method should be modified to increase its sensitivity.

In general, the enrichment of target molecules during subtractive hybridization requires that tester-tester hybrid molecules form during the reassociation step. Such molecules will include target-target duplexes. The rate at which double-stranded target duplexes form is a function of both the concentration of tester DNA and the duration of the hybridization step. Thus, using high concentrations of tester DNA in the hybridization step would promote this desired reaction. However, a second requirement of a successful subtractive hybridization experiment is that tester sequences common to both tester and driver populations, i.e., non-target sequences, will tend to form duplexes with driver rather than with the complementary tester strands. To promote this outcome, an excess of driver DNA must be present during the hybridization step, thus providing an incentive to conserve materials by keeping the tester DNA concentration as low as possible. Accordingly, a balance must be struck between raising the tester DNA concentration to promote the formation of target-target hybrids, and minimizing the tester DNA concentration to maintain a high driver:tester ratio.

In theory, target-target duplex formation could also be enhanced by increasing the hybridization reaction time. However, long incubation times are counterproductive and moreover, DNA tends to break down after several days of incubation. Thus, a more practical approach to enhancing the enrichment of target sequences would be to modify the reaction conditions so that tester-tester hybrids could form more quickly and at lower concentrations.

To increase the rate of reassociation during subtractive hybridization, some investigators have employed the phenol emulsion reassociation technique (PERT) of Kohne et al. (*Biochemistry*, 16:5329–5341, 1977; U.S. Pat. No. 5,132,207). In this method, the rate acceleration is dependent upon an emulsion formed by the physical agitation of DNA, phenol, and a buffered salt solution. Kohne et al. observed that DNA would reassociate in 5%–95% phenol. In one experiment, Kohne et al. found that using 9% phenol enhanced the rate of *E. coli* DNA reassociation by about 4,000-fold, and in another experiment, using 7% phenol enhanced the rate of reassociation of non-repeated mammalian DNA by 25,000-fold (Kohne et al., 1977). The extent of kinetic enhancement varied with DNA concentration and was most pronounced at low DNA concentrations. Another advantage of PERT is that phenol depresses the Tm of DNA duplexes so that hybridization can take place at room temperature. However, Kohne et al. noted that PERT was limited in that reannealing would not occur unless an emulsion was present and stated that continuous agitation was required to obtain the desired rate enhancement. In U.S. Pat. No. 5,132,207 (Kohne and Kacian, 1992), alternative methods were proposed to avoid PERT's disadvantages.

Others have combined PERT with subtractive hybridization to identify a segment of DNA deleted in a boy with Duchenne muscular dystrophy (Kunkel et al., *Proc. Natl. Acad. Sci. USA*, 82:4778–4782, 1985). Using 7% phenol, Kunkel et al. used intermittent mechanical shaking to maintain an emulsion in the reassociation reaction over a five-day period. Other investigators have similarly combined subtractive hybridization with PERT to isolate various target DNA sequences, again employing long hybridization times and shaking to provide an emulsion. (Nishi et al., 1992; Mor et al., 1991; Shiloh et al., 1987; Devlin and Donaldson, CA 2072231).

Zeng et al. (*Nucleic Acids Res.*, 22:4381–4385, 1994) have proposed a variation of subtractive hybridization combined with PERT, which they called enzymatic degrading subtraction (EDS). This group modified tester DNA by incorporating thionucleotides into the termini of restriction fragments, thus protecting tester-tester duplexes from nuclease digestion that was applied after the reassociation step to eliminate tester-driver and driver-driver duplexes. Eight percent phenol was used to accelerate the rate of hybridization and reactions were agitated during the reaction.

Recently, a modified PERT method has been proposed in which the emulsion is maintained by cycling between low and high temperatures rather than by physical agitation (Miller and Riblet, *Nucleic Acids Res.*, 23:2339–2340, 1995). Above 55° C., phenol is soluble in aqueous solutions, but becomes less soluble as the temperature is lowered. When of the temperature of a phenol aqueous solution is lowered, a fine emulsion forms, which eventually will dissipate as the aqueous and organic phases separate. When this separation begins to occur, the emulsion can be reestablished by again raising and then lowering the temperature of the solution. However, the use of thermal-cycled PERT has not been reported in conjunction with subtractive hybridization.

SUMMARY OF THE INVENTION

It has now been discovered that by combining several improvements to RDA, including thermal-cycled PERT, one can perform selective enrichments using much smaller initial amounts of nucleic acid than is feasible with conventional RDA methodology. To reflect this scale reduction, this improved procedure is called "micro-RDA." Micro-RDA provides a significant decrease in experiment throughput time that permits far more thorough research studies to be performed within a given time frame. These advantages are obtained with no loss of sensitivity relative to conventional RDA. Some experiments have even suggested that when micro-RDA is used in conjunction with enhancements for lowering the background, sensitivity may be somewhat increased over conventional RDA.

A major advantage of micro-RDA is that it permits the experimenter to dramatically decrease the amount of tester DNA used for the hybridization step. Once the tester DNA concentration has been lowered, the concentration of driver can be lowered also, as the amount of driver needed is simply that amount required to provide an adequate driver:tester ratio. Thus, micro-RDA results in conservation of both driver and tester source material, as well as laboratory reagents. Accordingly, micro-RDA can be used to analyze samples not previously amenable to RDA analysis. For example, micro-RDA can be used to discover genes or transcripts that are expressed in small tissue samples or that are expressed only transiently, for example, genes sequentially expressed during development or virus infection. Micro-RDA also could be used to analyze genetic mutations or transcripts in needle biopsies, a technique in which a small number of cells is aspirated into a needle, usually to be analyzed under the microscope by a pathologist. Similarly, snipe biopsies from inflammatory bowel disease tissue can be monitored by micro-RDA to map the neoplastic progression of the disease by detecting the sequential appearance of key transcripts. In other instances, cells segregated by fluorescence activated cell sorting (FACS) can be analyzed using micro-RDA. For example, FACS-enriched cell populations could include small numbers of lymphocytes having rare cell surface markers, or virus-infected cells present at low levels, or even groups of cells corresponding to several stages in neoplastic progression. In other applications, micro-RDA can be used to analyze nucleic acids from biological fluid samples containing relatively small numbers of cells, such as synovial fluid, cerebrospinal fluid, and serum. Such fluid analyses may contribute to the discovery of viruses that until now have eluded identification, e.g., the viruses responsible for many cases of viral encephalitis. A most important application of micro-RDA is during early development where, e.g., the method could be applied to identify transcripts specific to the various stages of development, such as the blastula, gastrula, or neural fold stages, or even earlier stages where only a few cells are present.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The invention provides improved methods for enriching target nucleic acid sequences that are present in a first source of nucleic acid but absent from a second source of nucleic acid. In the first step, amplicon DNA to be used as tester DNA is prepared from the first source of nucleic acid, which is DNA or RNA that contains the target nucleic acid sequences, and also from the second source of nucleic acid, which is DNA or RNA lacking the target nucleic acid sequences. Amplicon DNA from the first source is used as tester DNA, while amplicon DNA from the second source is used as driver DNA. When RNA is the source of nucleic acid, amplicon preparation is preceded by a step in which the RNA is converted to cDNA. Tester amplicon DNA and driver amplicon DNA are combined, melted by heating or by another method, and the two amplicon DNAs are coincubated in a reannealing reaction mixture containing an excess of driver amplicon DNA in an aqueous mixture that contains phenol. Reannealing, also known as reassociation or hybridization, is a reaction in which two strands of nucleic acid having complimentary base sequences form doublestranded molecules called hybrids or duplexes. During the reannealing step, the phenol is sustained in emulsion in the reaction mixture by alternatively heating the mixture to a temperature sufficient to dissolve most or all of the phenol, typically at least to about 65° C., and then cooling the mixture to a temperature at which the phenol becomes substantially insoluble, usually at least to below 37° C., and more typically at or below 25° C. By "substantially insoluble" is meant that a sufficient amount of phenol becomes insoluble to form a fine emulsion. The higher of the two incubation temperatures must not exceed the temperature at which DNA duplexes that have formed will melt. The optimal amount of phenol for this reaction mixture is about 11% to 13%, volume/volume, and most preferably about 12% by volume. A sufficient concentration of tester DNA is provided so that at least a portion of the reannealed DNA comprises tester-tester hybrids consisting of target nucleic acid sequences. After the reannealing step, the tester-tester hybrids are selectively amplified to obtain enrichment of the target nucleic acid sequences. The selective amplification step may be performed conventionally, such as by using the method described in Lisitsyn et al. (1993), which is hereby incorporated by reference.

By "tester" is meant a nucleic acid (DNA or RNA) taken from a source that contains the target sequences whose enrichment is desired. Sources of tester or driver nucleic acid may be procaryotic, eucaryotic, or viral. The tester amplicon DNA can be prepared from a cDNA population wherein the sequences of interest correspond to cellular or pathogen transcription products or, alternatively, the tester amplicon DNA can be prepared from genomic DNAs extracted from viruses, bacteria, or from cells or tissues that contain a target sequence of interest. Driver amplicon DNA is prepared from a source that lacks the target sequences, but that otherwise is similar in sequence composition to the tester nucleic acid. Preferably, the driver nucleic acid will contain all of the sequences in the tester nucleic acid except for the target sequences.

The term "amplicon," as pertains to the invention, refers to a sample of DNA prepared for subtractive hybridization by means of first cutting a sample of DNA (or cDNA) with a restriction endonuclease to produce smaller pieces of DNA known as "restriction fragments," then ligating the 5' termini of the resulting restriction fragments to an adapter oligonucleotide that recreates the restriction endonuclease site and also is copied in later steps by TAQ polymerase to provide sequences for hybridizing to a PCR primer. Methods for designing and ligating these adapter oligonucleotides are described in Lisitsyn et al. (1993). Adapter oligonucleotides typically are 24 bases in length, but longer or shorter adapters can be used. Adapter oligonucleotides generally are not phosphorylated; thus, because ligase requires a phosphate group, only the 5' terminus of each restriction fragment strand will ligate to an adapter oligonucleotide. Generally, both tester and driver DNA amplicons are prepared by digesting with the same restriction endonuclease. For example, cDNA can be digested with Dpn II, which cleaves outside of a 4-base pair recognition site for the enzyme. When genomic DNA rather than cDNA is used, the restriction endonuclease selected is generally one that cleaves at a 6-base recognition site. However, when analyzing genomic DNA from organisms with small genomes, e.g., bacteria, restriction endonucleases with 4-base recognition sites can be used.

After adapters are ligated to the restriction endonuclease-treated DNA, the protruding 5' ends are copied using TAQ polymerase, thus appending sequences complementary to the adapters to the 3' ends of the opposing strands. As a result, each strand now contains the adapter sequence at its 5' end, and a sequence complementary to the adapter at its 3' end. Then, an oligonucleotide containing the same sequence as the adapter is used as the primer in a PCR reaction that uses short thermal cycling times designed to favor the amplification of products that are less than 1 kb in length. As both strands contain a primer binding site, this amplification is exponential. The products of this PCR amplification step constitute the "amplicon" used in subsequent steps of subtractive hybridization.

Adapters are removed from both tester and driver amplicons by cleavage with the restriction endonuclease originally used to generate the fragments, and the adapters are physically separated from the amplified DNA. This can be done by any effective method, but most preferably is done by chromatography on Sephadex or using a QIAquick spin column (Qiagen). New adapter oligonucleotides with different sequences are then ligated to the tester but not the driver amplicon DNA.

For the first round of micro-RDA, a driver amplicon without adapters and a tester amplicon with new adapters are mixed, melted to disrupt existing duplexes, then reannealed under conditions that promote hybrid formation. For first round hybridization reactions, the molar ratio of driver to tester (D:T ratio) during reannealing generally is between about 10:1 to 1000:1, and more typically is about 100:1 to 300:1. Under these conditions, heteroduplexes of driver:tester hybrids are kinetically favored over the reformation of non-target homoduplex tester:tester hybrids. Thus, tester sequences common to both driver and tester populations are preferentially driven into driver:tester duplexes. "Selective amplification" is defined here to encompass three successive reactions that follow the hybridization step. These are a PCR amplification, a mung bean nuclease digestion, and another PCR amplification. In selective amplification, it is understood that only the DNA used as tester, i.e., the DNA present at the lower concentration during the prior hybridization step, will possess sequences at both ends that can anneal with PCR primers. Thus, the driver DNA, even when present in duplex form, is not subject to exponential PCR amplification. Thus, PCR amplification results in selective enrichment of target DNA.

Selective amplification is initiated with a "hot start" step that includes TAQ polymerase and nucleotide substrates, but excludes oligonucleotide primers. This permits the polymerase to copy the protruding 5' adapter sequences onto the 3' end of the opposing complementary strand to ensure exponential amplification of tester-tester duplexes during PCR. Following the hot start, the DNA duplexes are melted, and primers complementary to the tester adapter sequence are used to prime DNA synthesis by TAQ polymerase with about 10–15 thermal cycles. The resulting exponential amplification of tester-tester duplexes is the basis for the selective enrichment of target-target duplexes, which will constitute the majority of tester-tester duplexes present in the reaction mixture. Driver:tester templates have adapters on only one strand and thus only one strand of such duplexes can be copied by the polymerase. Hence, driver:tester duplexes are amplified linearly rather than exponentially. Driver:driver duplexes have no adapters, and thus are not amplified.

After the first PCR step of selective amplification, driver and tester molecules that failed to reanneal or that were produced during linear amplification remain single-stranded, while the products of tester-tester duplex amplification are double-stranded. In the second phase of selective amplification, mung bean nuclease is used to digest these single-stranded species to prevent them from interfering in later steps. Selective amplification is completed by another PCR amplification, this time with about 15–20 cycles.

One cycle of hybridization and selective amplification is considered to be a single "round" of micro-RDA and the DNA products of such a round are referred to as "difference products." While a great enrichment of target molecules is accomplished in the first round of micro-RDA, additional enrichment may be desired. If so, a second, third, and fourth round of RDA can be performed before the difference products are finally purified and cloned for further analysis. To prepare first round difference products for a second round of RDA, the adapters are removed from the difference products and a new adapter is ligated to the difference products' 5' termini. This new adapter has a sequence different from all of the adapters used in earlier steps. To perform a second round of RDA, the first round difference products having new adapters are hybridized to a freshly added excess of driver amplicon DNA, and the selective amplification process is repeated. For the hybridization step in a second round of RDA, higher D:T ratios are generally used than are used for the first round. Typically, second round D:T ratios will range from between 100:1 to 10,000:1, and most typically will be about 1000:1. If a third or fourth round is performed, D:T ratios are again increased, typically ranging between 10,000:1 and 100,000:1.

Hybridization reactions are generally conducted in a 50 µl volume that contains 100 ng of driver amplicon and between 1 pg and 1 ng of tester amplicon or difference products. If desired, larger or smaller volumes can be used. Typically, progressively less tester DNA is used for the hybridization steps in second, third, and fourth rounds of selective amplification. For example, the first round might utilize 1 ng of tester, the second round 100 pg, and the third 10 pg of tester DNA. For each round, about 100 ng of driver DNA is usually used, although the amount of driver can be manipulated as needed.

The hybridization reaction mixtures are incubated in a thermal cycler such as that used for PCR. Enough phenol is provided during the hybridization step so that a fine emulsion forms when the temperature is first raised to a temperature sufficient to dissolve some of the phenol, then dropped to a temperature at which the dissolved phenol becomes insoluble. For these purposes, a convenient range of phenol concentrations is between 11% and 13% (vol/vol). At the onset of a hybridization reaction, the temperature is raised to 100° C. for ten minutes to denature (melt) the DNA duplexes. Thereafter, the temperature is cycled between a temperature of about 25° C. or below for 15 minutes and a second temperature of about 65° C. for two minutes. At the higher temperature, the phenol dissolves in the aqueous buffer. When the temperature is dropped to the lower temperature, an emulsion forms and remains relatively stable throughout each 15-minute period, which is the period during which hybrids form. Optimally, the reaction mixtures are held at a hybridization temperature of about 25° C. until the two phases just begin to separate. If desired, longer hybridization periods may be used, although phase separation may occur if this is done. When the temperature is raised again to about 65° C., the phenol is driven into solution without melting the hybrids that were formed during the prior hybridization period. The cycling is repeated for about 0.5 h to 24 h, but most preferably for about 1 hour.

Micro-RDA offers numerous advantages over conventional RDA procedures. The most notable advantages are that by using the improvements described herein, one can perform RDA experiments using substantially less DNA and in a much shorter time frame than by using the conventional method. One advantage of using less DNA is that reactants can be purified on QIAquick spin columns between steps instead of being subjected to organic extraction and ethanol precipitations between reactions. Not only does the use of spin columns save time, but it also results in lower backgrounds, and thus greater sensitivity. QIAquick columns, with their limited capacity, are impractical in standard RDA, which typically calls for about 40 µg of driver amplicon DNA per hybridization reaction.

In addition, the subject invention offers ways of removing ribosomal RNA (rRNA) from a population of RNA molecules prior to RDA analysis. It has been observed that when total unfractionated RNA is used as a source of tester nucleic acid in RDA, characteristic rRNA-derived bands usually appear in gels displaying the tester amplicon. These rRNA-derived bands may compete with target molecules for primer, TAQ polymerase, and nucleotide substrates, thus may suppress the detection of scarce target molecules. When analysis of polyadenylated mRNA is desired, oligo(dT) selection can be used to prepare a purified fraction of messenger RNA prior to cDNA synthesis. However, oligo(dT) selection does not recover all mRNA, hence removal of rRNA may be a desirable alternative to oligo(dT) selection. Moreover, it may be desirable to analyze RNAs other than mRNA, such as bacterial transcripts, histone mRNAs, small nuclear RNAs, non-polyadenylated viral RNA genomes, or even degraded mRNA from autopsy samples, which is too fragmented to be effectively purified by oligo(dT) selection.

The improvements offered herein also facilitate the use of a strategy called "serial RDA." In serial RDA, one performs an initial RDA experiment, recovers the target sequences, and adds them back to the driver in a subsequent RDA experiment that is otherwise identical to the first. This strategy permits the selective amplification of scarce target sequences against a background of abundant targets that otherwise would be preferentially selected. Using conventional RDA methodology for a serial RDA strategy is cumbersome and impractical compared to the ease with which serial RDA can be performed when micro-RDA is used.

In addition, the invention provides a method called "difference product comparison by subtraction" (DPCS) for enriching target nucleic acid sequences that are shared by two or more populations of nucleic acid. In the initial stage of DPCS, one prepares amplicon DNAs from two sources of tester nucleic acid, using a third nucleic acid as the source of driver. For example, the first two sources could be derived from a cell line infected with two different viruses, whereas the third source was the same cell line not infected with either virus. By manipulating RDA as illustrated in Example 10, one can selectively amplify and recover transcripts expressed in both infected cell lines, but which are not expressed in the uninfected cells. Thus, one could identify cellular genes whose transcription was triggered non-specifically by viral infection.

The following examples are offered to illustrate the method of the present invention and are not intended to limit the means and ways by which these improvements can be applied.

EXAMPLE 1

Detection of Spiked Target DNA Using PERT with RDA

The performance of any subtractive cloning procedure is dependent upon the efficiency of DNA reassociation during the hybridization step. Traditional DNA hybridization protocols control the extent of DNA reassociation primarily by manipulating the DNA concentration and the length of the incubation. Thus, maximal reassociation is traditionally obtained by using long hybridization times and high DNA concentrations.

An experiment was performed to determine whether combining thermal-cycled PERT with RDA would make it possible to obtain a high degree of target enrichment while simultaneously reducing the overall time required to perform the procedure.

In the standard PERT procedure, the mechanism of rate acceleration relies on physical agitation to create an emulsion of a mixture of DNA, phenol, and buffered salt solutions. This procedure has remained relatively obscure and is apparently beset with technical difficulties in forming and maintaining an emulsion by physical agitation. Miller and Riblet (1995) have proposed a more effective means than agitation for maintaining an emulsion during PERT hybridization. Above 55° C., phenol up to about 12% (vol/vol) is soluble in an aqueous phosphate buffer, but is insoluble at lower temperatures. When the temperature of a phenol solution is lowered, the phenol comes out of solution by first forming a fine emulsion, which eventually dissipates as the aqueous and organic phases separate. Thus, when the temperature of such a phenol solution is cycled between 65° C. and 25° C., the phenol alternates between an emulsion and a dissolved state. Thus, by alternately raising and lowering the temperature during hybridization, phase separation can be avoided by repeatedly re-establishing the emulsion throughout the hybridization incubation period.

Amplicon Synthesis

The DNA used for this experiment was derived from approximately 1 g of human autopsy meningeal membrane tissue from an amyotrophic lateral sclerosis patient. Driver and tester DNAs were identical except that the driver DNA was spiked with two different exogenous DNA molecules intended to serve as target sequences. The human brain DNA was prepared by a standard protocol involving proteinase K digestion (Sambrook et al., *Molecular Cloning, 2nd Ed.*, Cold Spring Harbor Press, 1989, which is hereby incorporated by reference). One of the target DNAs was lambda bacteriophage genomic DNA (New England Biolabs), spiked at the equivalent of 10 viral genomes per haploid genome of human tester DNA. The other target DNA was adenovirus-2 genomic DNA (New England Biolabs), spiked at the equivalent of one viral genome per human haploid genome.

Amplicon production was performed essentially as described by Lisitsyn et al., (1993). Prior to the initial digestion with restriction endonuclease, 6 µg of tester DNA was spiked with 100 pg of adenovirus DNA and 1 ng of lambda bacteriophage DNA. Six µg of driver DNA and spiked tester DNA were each digested for 16 hours with 50 units of Bgl II (New England Biolabs) in a 100 µl reaction. After digestion, reaction mixtures were purified by phenol extraction and ethanol precipitation. RBgl 24 and RBgl 12 oligonucleotide adapters were annealed to the digested DNA, DNA ligase (Boehringer-Mannheim) added overnight at 15° C., and PCR performed as described (Lisitsyn et al., 1993). After the PCR step, both of the resulting amplicons were digested with Bgl II to remove the adapter oligonucleotides. A new set of Bgl II adapters, the JBgl set described in Lisitsyn et al. (1993), were ligated to the tester amplicon DNA, but not to the driver amplicon DNA. One round of RDA was performed, following the standard RDA protocol of Lisitsyn et al. (1993). The adapters were removed from the resulting first round difference product by Bgl II digestion, then NBgl adapters (Lisitsyn et al., 1993) were ligated to the product.

To evaluate the efficacy of thermal-cycled PERT, six pairs of RDA experiments were set up (see Table 1). Within each pair, the reaction components were identical except that the source of tester DNA was slightly different. The first member of each pair (odd-numbered tubes) utilized the amplicon DNA as described in the previous paragraph, and the second member of each pair (even-numbered tubes) utilized the first round difference products described also in the previous paragraph. The above-described driver amplicon served as the driver DNA in all twelve reactions. The amounts of tester and driver DNAs added to each of the twelve reaction tubes are shown in Table 1.

TABLE 1

PERT Trial Design

| | Source of Tester DNA | | Amount of Tester DNA | Amount of Driver DNA |
|---|---|---|---|---|
| 1. Standard RDA | Tester amplicon | | 400 ng | 40 µg |
| 2. Standard RDA | First round difference product | | 50 ng | 40 µg |
| 3. PERT RDA | Tester amplicon | | 400 ng | 40 µg |
| 4. PERT RDA | First round difference product | | 50 ng | 40 µg |
| 5. PERT RDA | Tester amplicon | | 80 ng | 8 µg |
| 6. PERT RDA | First round difference product | | 10 ng | 8 µg |
| 7. PERT RDA | Tester amplicon | | 20 ng | 2 µg |
| 8. PERT RDA | First round difference product | | 2.5 ng | 2 µg |
| 9. PERT RDA | Tester amplicon | QIAquick | 20 ng | 2 µg |
| 10. PERT RDA | First round difference product | QIAquick | 2.5 ng | 2 µg |
| 11. PERT RDA | Tester amplicon | QIAquick | 2 ng | 2 µg |
| 12. PERT RDA | First round difference product | QIAquick | 250 pg | 2 µg |

This experimental design addressed several questions. Reactions 1 and 2 were identical to numbers 3 and 4, except that the latter pair contained phenol in the reaction mixture, as did samples 5–12. The second, third, and fourth pairs contained decreasing amounts of DNA, but among pairs had the same D:T ratios, i.e., numbers 3, 5, and 7 had a D:T ratio of 100:1, and numbers 2, 4, and 6 had a D:T ratio of 800:1. The fifth and sixth pairs were variations of the fourth pair. The fifth pair (9 and 10) were identical to the previous pair (7 and 8), except that 9 and 10 were passed through a QIAquick spin column (QIAgen, Chatsworth, Calif.) between the amplicon preparation step and the hybridization step to remove the digested oligonucleotide adapters. Samples 11 and 12 were the same as 9 and 10, except that 11 and 12 received 10-fold less tester DNA, and hence had tenfold higher D:T ratios.

PERT Hybridization

Hybridizations were conducted in a volume of 50 µl, and contained 1.5M NaSCN, 120 mM PB, 10 mM EDTA, and 8% phenol (Miller and Riblet, 1995). Reactions were covered with 30 µl of mineral oil. To initiate hybridization, the reaction mixtures were heated at 100° C. for 10 minutes, then placed on ice. The samples were then placed in a thermocycler and cycled between 65° C. for two minutes, and 25° C. for 15 minutes (Perkin-Elmer 480 thermal cycler); cycling was continued overnight. The next morning, emulsions were present in only two of the ten reaction tubes that contained phenol.

In an effort to improve emulsion stability, 2 µl of ultrapure phenol (Sigma) was added to samples 3–12, thus raising their phenol concentration to 12%. Again, all twelve samples were heated to 100° C. for 10 minutes and the hybridization was repeated overnight. The next morning, emulsions were present in sample numbers 3–12, thus the higher concentration of phenol resolved the problem of maintaining stable emulsions during the hybridization.

All of the reactions that contained phenol (numbers 3–12) were purified in preparation for selective amplification by chloroform extraction, which was followed by desalting with QIAquick spin columns. The remaining steps in the selective amplification were performed essentially as described by Lisitsyn et al., 1993. After the mung bean nuclease step, reaction mixtures were diluted with 4 volumes of 50 mM Tris, pH 8.9, and heated at 98° C. for five minutes to inactivate the nuclease. Second PCR amplifications were performed using 40 µl of mung bean-treated DNA as template. The odd-numbered samples each underwent 15 cycles of amplification, and the even-numbered samples underwent 17 cycles. After the second PCR amplification, the resulting difference products were visualized on a 2% agarose gel, shown in FIG. 1.

Figure 1:
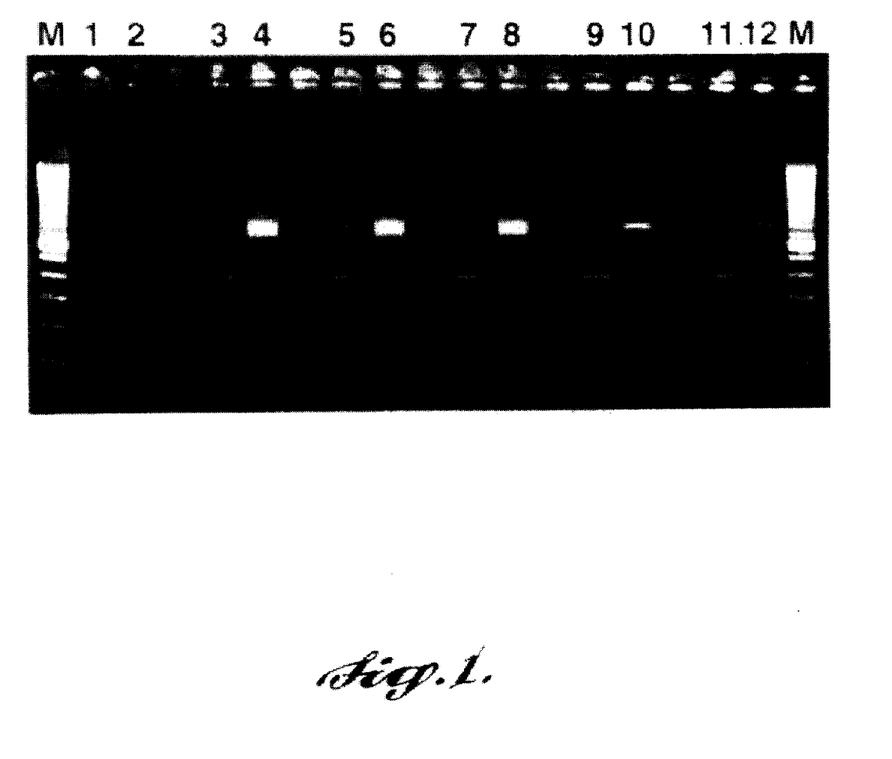
FIG. 1 depicts the final RDA difference products obtained in the experiment described in Example 1.

In a successful enrichment, the lambda phage target was expected to yield a 651 base pair DNA product, whereas the adenovirus-2 target was expected to yield a 351 base pair and a 275 base pair product. As seen in FIG. 1, at least some of the anticipated bands were observed in all of the samples except for 1 and 2. Samples 1 and 2 were hybridized under standard conditions without phenol added. Thus, these results suggest the possibility that the sensitivity of RDA combined with PERT may be greater than the sensitivity of standard RDA, although definitive experiments to address this possibility have not been conducted.

The results of this experiment indicated also that no loss in sensitivity resulted from reducing the amount of driver while holding the D:T ratios constant. This was apparent from comparing the results of the second, third and fourth pairs of hybridizations (FIG. 1). Thus, with a constant D:T ration, the same ability to detect targets was obtained whether 40 µg, 8 µg, or 2 µg of driver were utilized during the hybridization reaction, thus illustrating that using PERT permits RDA to be scaled down at least 20-fold.

EXAMPLE 2

Suppressing the Generation of Ribosomal RNA Product

To facilitate the analysis of unfractionated RNA populations, as, for example, to analyze small nuclear RNAs or non-polyadenylated viral transcripts, it would be advantageous to apply RDA directly to cDNA populations derived from total cellular RNA. However, 90% or more of total cellular RNA is ribosomal RNA (rRNA). Thus, a set of intense bands derived from rRNA template are seen when amplicons generated from total cellular RNAs are displayed on an agarose gel. In experiments in which no target molecules were present in the tester amplicon, these rRNA products often persisted through several rounds of hybridization and selective amplification. This persistence suggests that the rRNA products that constitute the majority species in amplicons could compete with target molecules for TAQ polymerase, PCR primers, and nucleotide substrates, thus reducing the extent to which tester-tester hybrids are amplified. Thus, preventing the generation of rRNA products during RDA should result in a substantial increase in the overall sensitivity of target detection.

Unwanted rRNA difference products could derive from either the rRNA encoded by nuclear genes, or that encoded by mitochondrial DNA. Hence, any strategy for removal of rRNA will target the mitochondrial-encoded sequences as well as those encoded in the nucleus.

In the experiments described below, the net gain in RDA sensitivity is evaluated by measuring the recovery of titrated amounts of spiked target RNAs that were added to the tester RNA prior to the initial cDNA synthesis. After RDA, the final difference products are analyzed on agarose gels, and the presence or absence of the spiked target bands provides a measure of whether or not the tested protocol provided sufficient sensitivity to detect various levels of spiked targets.

a. Blocking Reverse Transcription of rRNA Template

An analysis of the amplified bands generated from rRNA indicated that based on the sequences of the rRNAs, only a relatively small subset of the fragments that could have arisen from these RNAs were actually represented in amplicons. This probably was because areas of strong secondary structure on the rRNA inhibited reverse transcription of all but a few open regions during cDNA synthesis. Accordingly, blocking reverse transcription at just a few specific sites on the rRNA molecules should eliminate the cDNA synthetic activity that is responsible for producing the rRNA fragments that are abundantly represented in amplicons.

Thus, the synthesis of cDNA from rRNA templates is blocked by designing oligonucleotides that are complementary to the open regions of rRNA (i.e., regions not involved in intramolecular duplexes, such as hairpins) in the areas defined by the sequences of the major ribosomal RNA products detected in the amplicons. The secondary structure of rRNA is highly conserved, thus the locations of open regions and regions involved in secondary structure are well known and have been mapped (e.g., Lasater et al., *Biochemistry*, 27:4687–4695, 1988; Noller, *Ann. Rev. Biochem.*, 53:119–162, 1984). A molar excess of oligonucleotides complementary to the amplified open regions is added prior to the first strand cDNA synthesis reactions. Amounts and combinations of blocking oligonucleotides are compared to determine the best conditions for suppressing the reverse transcription of the rRNA-derived products.

b. Physical Removal of rRNA Prior to Reverse Transcription

The objective of this approach is to remove ribosomal RNA from total cellular RNA before adding the reverse transcriptase by employing a "capture-subtraction" strategy.

First, cDNA fragments of the ribosomal RNA 12S, 16S, 18S, and 28S sequences are cloned in any convenient vector. Large quantities of the cloned fragments are prepared, and the resulting DNAs are either covalently attached to glass beads or are attached to streptavidin-coated beads via a biotin label incorporated into the cloned DNA, such as by using streptavidin-coated Magnetic Porous Glass (CPG, Lincoln Park, N.J.), following the protocol of Lolarova and Hengerer (*BioTechniques*, 20:198–200, 1996). Total cellular RNA is brought into contact with the glass beads under conditions that promote the formation of duplexes between the rRNA and the anchored cloned DNA. The fraction of RNA that does not bind to the beads is recovered and used to prepare cDNA, which in turn is used to prepare amplicons for RDA.

Alternatively, instead of linking the cloned ribosomal DNA to beads, it is biotinylated and hybridized in solution with cellular RNA. The hybridized nucleic acid is then exposed to a solid matrix to which streptavidin is attached, such as the beads available from CPG. Alternatively, the solid matrix to which streptavidin is attached could be glass beads, nylon, polystyrene, Sephadex, or other suitable material. Duplexes containing rRNA become bound to the anchored streptavidin by virtue of their biotinylated DNA component. The unbound fraction is recovered and used to prepare amplicon DNA. Other methods can be devised for the physical removal of rRNA.

c. Using Poly(A)-selected RNA as Template for Reverse Transcription

Where eucaryotic cells are the subject of study, one option for improved sensitivity in RDA is to create cDNA from only that fraction of total cellular RNA that contains 3' polyadenylic acid, i.e., a poly(A) tail. Most eucaryotic mRNA is polyadenylated, as are most transcription products of viruses that infect eucaryotic cells. Conventional methods can be used to select the polyadenylated fraction from preparations of cellular nucleic acids (e.g., by applying methods described in Sambrook et al., 1989, which is hereby incorporated by reference).

To test the degree to which this approach could improve sensitivity, total cellular RNA from VERO cells (African green monkey kidney cells, ATCC No. CCL 1586) was spiked with 0.1 to 100 copies per cell with polyadenylated RNAs transcribed in vitro from cloned cDNA fragments corresponding to chicken spermatogenesis-specific transcripts. A portion of the spiked RNA was poly(A) selected. Both the selected and the unfractionated RNAs were transcribed into cDNA which in turn was used as tester DNA in RDA reactions where the source of driver was the corresponding unspiked VERO RNA, i.e., either oligo(dT)-selected or unfractionated. Phenol was used during the hybridization step (see Example 1). Products from the 100 copy/cell spike were visible in the poly(A)-selected sample but not in the unfractionated sample after only one round of hybridization and selective amplification. This result demonstrated that the oligo(dT) selection step indeed provided a significant improvement in RDA sensitivity. Moreover, this level of sensitivity after only one round of RDA has not been reported in prior experiments using total RNA.

EXAMPLE 3

Optimization of Driver:Tester Ratio

Because PERT is especially effective in accelerating hybridization rates when DNA is present at low concentrations (Kohne et al., 1977), using PERT should substantially decrease the amount of tester molecules required in an RDA hybridization reaction. If so, the D:T ratio would be effectively increased, and one could if desired reduce the amount of driver DNA as well. Thus, one would conserve both tester and driver DNAs that might be in short supply. The results shown in Example 1 suggested that lowering the tester DNA concentration had no adverse effect on target enrichment, as similar results were observed when the amounts of tester and driver were progressively scaled down in samples 3–8.

Additional experiments were performed to confirm the results in Example 1 and to determine whether tester DNA concentration could be reduced even further. For these experiments, peripheral blood lymphocyte total cellular RNA was spiked with MS2bacteriophage RNA to levels equivalent to 1000, 100, 10, 1, and 0.1 molecules of MS2 RNA per cell, assuming 10 pg of total RNA per cell. Both spiked and unspiked RNA was transcribed into cDNA, extracted with phenol, and precipitated with ethanol.

After rehydration, the tester (spiked) and driver (unspiked) cDNAs were digested with MspI and purified by QIAquick chromatography. Initial RDA experiments, using thermal cycled PERT, were conducted in which the D:T ratios were titrated between 100:1 and 10,000:1. These results indicated that D:T ratios in the 1000:1 to 10,000:1 range during the first three rounds of RDA indeed resulted in more efficient recovery of target molecules and lower levels of background products than when the conventional RDA ratios (100:1, 800:1, and 400,000:1) were used.

In subsequent spiked target experiments, the D:T ratios were titrated in both the first and second round hybridization reactions as follows:

TABLE 2

| First Round Hybridization | Second Round Hybridization | Third Round Hybridization |
| --- | --- | --- |
| 100:1 | 1,000:1 | 10,000:1 |
| 100:1 | 3,000:1 | 10,000:1 |
| 100:1 | 10,000:1 | 10,000:1 |
| 300:1 | 1,000:1 | 10,000:1 |
| 300:1 | 3,000:1 | 10,000:1 |
| 300:1 | 10,000:1 | 10,000:1 |
| 1,000:1 | 1,000:1 | 10,000:1 |
| 1,000:1 | 3,000:1 | 10,000:1 |
| 1,000:1 | 10,000:1 | 10,000:1 |

These experiments showed that optimal sensitivity occurs when the D:T ratio in the first round hybridization reaction is in the 100–300:1 range. For the second hybridization reaction, equivalent sensitivity was seen in the 1,000–10,000:1 range, although the amount of background signal was less at a ratio of 10,000:1. Thus, an optimal protocol would have the driver:tester ratios set at 100–300:1 for the first round of RDA, 1,000–10,000:1 for the second round, and 10,000:1 for the third round. This represents a significant departure from the corresponding 100:1, 800:1, and 400,000:1 ratios used in conventional RDA procedures.

These results suggest that D:T ratios can be tailored to the requirements of particular experiments. For example, the lower sequence complexity of bacterial systems can support higher D:T ratios which in turn permit experiments to be completed with only one or two rounds of hybridization and selective amplification. The greater sequence complexity of higher eucaryotic RNA means that in selecting a D:T ratio, one must balance efficiency against sensitivity, i.e., the speed at which abundant targets can be recovered, and the ability to detect scarce targets. In essence, one can use a high D:T ratio for a quick look at abundant RNA species, or one can use a lower D:T ratio in a slightly more laborious search for low abundance targets.

EXAMPLE 4

Optimization of Phenol Emulsion Formation

A study of the parameters that affect the formation and stability of a phenol emulsion revealed that the emulsion tends to be unstable at low DNA concentrations. Tests have indicated that emulsion stability becomes problematic if driver concentrations are below 2 µg/ml. Thus, the standard hybridization reaction in the present formulation of this method now consists of a 50 µl volume that contains 100 ng of driver amplicon and between 1 ng and 1 pg of tester amplicon or difference products, i.e., a DNA concentration of about 2 µg/ml. These DNA concentrations consistently support a stable emulsion, and the only apparent limit to the reaction scale is the number of target molecules that are present during the hybridization step. For example, if an average eucaryotic cell contains 10 pg of RNA, one would risk losing scarce target sequences if less than about 20 pg of tester amplicon DNA were used for the first round hybridization reaction.

EXAMPLE 5

Replacement of Organic Extraction Cleanup Steps with Chromatography

Much of the conventional RDA procedure calls for organic extractions and ethanol precipitations to desalt and remove proteins following each of the enzymatic reactions. The time required for these extractions and precipitations limits the number of samples that can be processed in a given time period. Accordingly, for micro-RDA, every organic extraction step in the conventional protocol has been replaced by chromatography either using a Sephadex G25 column or a QIAquick Spin column. Not only does this modification save time, but unlike organic extractions and ethanol precipitations, it ensures the removal of the cleaved adapter molecules generated by the restriction endonuclease digestions. Furthermore, chromatography is more amenable to high throughput automation than organic extractions, which must be performed in a fume hood. Further increases in throughput can be obtained by adapting this modification to a 96-well format with at least some automated steps performed by a robotic device. This is presently feasible as a chromatographic reagent similar to QIAquick is available in 96-well format from Advanced Genetic Technologies Corporation (Gaithersberg, Md.).

EXAMPLE 6

Optimization of Hybridization Time

It seemed possible that the rate acceleration achieved by using PERT during hybridization would dramatically reduce the time required for the hybridization reaction. To investigate this possibility, a first experiment using two separate model systems was designed to compare the recovery of high copy number spiked target molecules using different hybridization times. In the fist model, peripheral blood lymphocyte RNA was spiked with the MS2 bacteriophage RNA at a level equivalent to 1,000 copies per cell and MspI was used as the restriction endoneuclease. In the second model system, VERO cell RNA was spiked with MS2 RNA at a level equivalent to 100 copies per cell, and Dpn II was used as the restriction endonuclease. For both model systems, amplicons were prepared, with the spiked RNAs being used as testers, and the corresponding unspiked RNAs being used as drivers. One round of RDA was performed in which the hybridization times were either 0.5, 1, 2, 4, or 20 hours. Surprisingly, in both model systems, the recovery of target was independent of the length of the hybridization incubation.

Further experiments demonstrated that even when targets were present at a low copy number per cell, there was equal sensitivity whether the reannealing step was for one hour or overnight. For this experiment, peripheral blood lymphocyte RNA was spiked with varying amounts of MS2 RNA, ranging from equivalents of 0.1 to 1,000 copies per cell. RDA was performed using the spiked RNA as the source of tester, and the unspiked RNA as the source of driver. A hybridization time of 20 hours was compared with a 1 hour hybridization time that included three thermal cycles. Three rounds of RDA were performed. For both hybridization protocols, a similar recovery of MS2 fragments was observed in the first, second, and third round difference products.

EXAMPLE 7

Micro-RDA

The following protocol incorporates into RDA the improvements described in Examples 1 and 3–6 and is otherwise optimized for maximal efficiency. Compared with standard RDA, these improvements make it possible to perform RDA experiments using far less nucleic acid and in a much shorter time period. The efficacy of the improvements described in Examples 3–5 is evident in the rate at which experiments can now be conducted using the optimized protocol. For example, using these improvements, 20 RDA experiments can easily be done in one week, in contrast to a reasonable rate for conventional RDA of five experiments in three weeks. This improved protocol is called "micro-RDA," which reflects the reduced scale and shortened throughput time of this new protocol. As more studies are completed, micro-RDA can be further refined to improve its efficiency with respect to conservation of both time and reagents. Amplicons are prepared from a DNA or RNA source essentially as described in Example 1. The remaining steps are carried out as follows.

1. Hybridization

Set-up:

Dilute driver to 100 ng/μl

Dilute tester ligation to 1 ng/μl (100 pg/μl for 2nd round; 10 pg/μl for 3rd round)

Add 1 μl tester and 1 μl driver DNA to 0.65 ml polypropylene tube

Premix: (Per each tube):

1 μl of 0.5M EDTA

6 μl of 1M PB (equimolar mono- and di-basic sodium phosphate)

6 μl of ultrapure, unbuffered phenol

15 μl of 5M NaSCN

20 μl water

To assemble hybridization reactions:

Melt phenol at 65°–70° C.

Assemble all other components in heat block at >65°

Add phenol to premix, and keep at >65°

Make sure that the premix is homogeneous, i.e., the phenol is completely dissolved in the aqueous phase, and the total volume is a uniform emulsion.

Add 48 μl premix to each tube (it may be necessary to agitate the premix every 10 seconds or so to keep it homogeneous while dispensing it)

Cover each reaction mixture with 30 μl mineral oil

PERT cycling:

100° C. 10 minutes (to melt driver and tester amplicon DNAs)

Three cycles of:
25° C. 15 minutes
65° C. 2 minutes

Ramp down to 25° C.

2. Selective Amplification

1) DNA purification:

Extract the hybridization reaction with 100 μl chloroform to remove phenol.

Purify DNA using QIAGEN's QIAquick Spin PCR Purification Kit (hereafter, QX), as per manufacturer's instructions, except elute the DNA into a final volume of 20 μl water. To do this add 20 μl water to the membrane, wait for 2 minutes, then spin for 2 minutes to recover the entire volume.

2) 1st Selective amplification (50 μl reaction):

20 μl DNA from previous QX elution

10 μl 5× PCR buffer (33 mM Tris-HCl, pH 8.8, 20 mM MgCl$_2$, 80 mM (NH$_4$)$_2$SO$_4$, 50 mM B-mercaptoethanol, 0.5 mg/ml bovine serum albumen)

0.64 μl nucleotides (25 mM each of dATP, dGTP, dCTP, and dTTP)

17.08 μl water 0.375 μl TAQ polymerase (5 units/μl, Boehninger Mannheim) diluted up to 1 μl Hot start by incubating at 72° C. for 5 minutes After hot start/fill-in, add 1.28 μl of 62 pm/μl oligonucleotide primer Perform PCR for 15 cycles with standard RDA parameters (Lisitsyn et al., 1993).

3) Mung bean nuclease digestion (20 μl volume):

QX purify all 50 μl of PCR, elute into 10 μl water

Prepare 2× MBN mix:

7 μl water

2 μl 10× MBN buffer (New England Biolabs)

1 μl MBN enzyme (10 units/μl, New England Biolabs)

Add 10 μl 2× MBN mix to each tube

Incubate at 30° C., for 30 minutes.

QX entire mung bean digest. To elute, add 30 μl water to membrane, wait 2 minutes, then spin as directed.

4) Additional rounds of selective amplification (100 μl volume):

10 μl QXed mung bean nuclease-treated DNA from previous step

20 μl 5× PCR buffer 1.3 μl nucleotides (25 mM each of dATP, dATP, dCTP, and dTTP)

2.5 μl 62 pm/μl oligonucleotide primer 65.4 μl water

Hot start with 0.75 μl TAQ polymerase

For second round, perform PCR for 15–20 cycles with standard RDA parameters.

For a third or fourth round, perform 20–25 cycles of PCR

Analyze difference products on a 2% agarose gel.

5) Adapter changes:

a) QX 50 μl of difference product from step (4). Elute in 50 μl water.

b) Digest difference product with restriction endonuclease in 50 μl total volume (for Dpn II, 1 hr. digestion time is adequate). Run agarose gel to ensure that digestion is complete.

c) Purify by QX twice, to remove cleaved adapters.

d) Quantify the amount of DNA in recovered samples using a TKO 100 mini-fluorimeter (Hoefer) to measure Hoechst 33258-treated product against a standard DNA solution.

e) Set up ligation:

100 ng purified difference product 7.5 μl 62 pm/μl 24-mer adapter oligonucleotide 7.5 µl 62 pm/µl 12-mer adapter oligonucleotide
3 µl 10× ligase buffer (Boehninger-Mannheim)
2 µl T4 DNA ligase (Boehninger-Mannheim)
water, up to 30 µl total volume
Incubate at 16° C. for >3 hours.
Perform additional rounds of RDA by repeating the hybridization and selective amplification steps.

EXAMPLE 8

Substitution of λ Exonuclease for Mung Bean Exonuclease

In the standard RDA protocol, the hybridization step is followed sequentially by selective amplification, a multi-step procedure that includes PCR amplification, mung bean nuclease digestion, and a second PCR amplification. The purpose of the mung bean nuclease digestion is to remove single stranded DNA, which includes driver DNA, and the single-stranded products of linear amplification. A more efficient approach would be to remove this unwanted DNA with an exonuclease derived from bacteriophage lambda, namely, λ exonuclease. The λ exonuclease catalyzes the stepwise release of mononucleotides from the 5' ends of double-stranded DNAs that have a terminal 5' phosphate group. Thus, following an RDA hybridization reaction, λ exonuclease should degrade all driver strands whether they are present in driver-driver or tester-driver duplexes. However, tester strands should not be digested by λ exonuclease. This is because while driver molecules have 5' phosphates, tester molecules do not (because the adapters ligated to their 5' ends have 5' OH groups). Thus, tester strands are resistant to λ exonuclease. Accordingly, if the hybridization mixture is digested with λ exonuclease, the only surviving products should be the double-stranded tester-tester hybrids and the single-stranded tester molecules left after the λ exonuclease has digested the driver strands of the driver-tester hybrids. Thus, using λ exonuclease should improve the selective amplification procedure by more effectively removing driver DNA, thereby increasing the sensitivity of the procedure.

In preliminary experiments, the relative efficacy of λ exonuclease and mung bean nuclease has been assessed. The results of the first experiment indicated that the two approaches were roughly equivalent in sensitivity. However, in subsequent experiments, digestion by λ exonuclease was not blocked completely by a 5' hydroxyl group, resulting in partial degradation of tester-tester duplexes. To solve this problem, adapter oligonucleotides are synthesized having polyethylene glycol blocking groups at their 5' ends. These modified adapter oligonucleotides are ligated to tester DNA, thus presenting λ exonuclease with a modified and possibly undigestable target. Other modifications can be applied to the adapter oligonucleotides to render them resistant to λ exonuclease. Alternatively, altering the components of the reaction buffer may render the 5' termini more resistant to digestion. Such modifications should make it possible to substitute λ exonuclease for mung bean nuclease.

EXAMPLE 9

Removal of 3' Adapters as Alternative to Adapter Changes

Adapter changes, which involve restriction endonuclease and ligase reactions, are among the slowest and most cumbersome steps required in any RDA protocol. In the standard RDA protocol, the initial PCR adapters used during amplicon preparation are removed prior to the first round of RDA because otherwise, each tester DNA strand entering the first round hybridization step would still have the initial adapter sequence at its 5' end, and would also have the complement to that same sequence at its 3' end. This intramolecular complementarity would lead to such molecules forming undesirable hairpins and networks during the first round hybridization step. More importantly, all of the tester strands would be subject to amplification during successive rounds of PCR, with there being no discrimination between target and non-target tester-tester molecules. To prevent these undesirable results, the initial adapters are cleaved off, and a different adapter sequence is ligated to the 5' ends of tester-tester duplex DNAs prior to the first round hybridization. For similar reasons, adapters are routinely removed and replaced with different adapters in between each successive round of RDA.

Elimination of the cumbersome adapter changes would further reduce the cost and amount of time required to perform RDA. One approach to eliminating adapter changes is to treat PCR products with a reagent that will preferentially remove the unwanted sequences from the 3' ends of amplified DNA strands, while leaving the 5' sequences of these same strands intact. This could be accomplished, for example, by use of an exonuclease that selectively digests the 3' ends of double-stranded DNA molecules. One such enzyme is *E. coli* exonuclease III, which removes mononucleotides stepwise from the 3'-OH termini of double-stranded DNA. Because it is nonprocessive, this enzyme typically generates populations of product molecules that have been resected to a similar degree.

Successful strategies for using exonuclease III will require steps to ensure that the resection does not proceed beyond the unwanted adapter complements. This may be accomplished, for example, by melting the amplicon PCR product, and annealing it briefly with a vast excess of an oligonucleotide, e.g., the PCR primer that will hybridize with the 3' adapter sequence. Thereafter, only the 3' ends of the amplicon strands will exist in a double-stranded form. Exonuclease III is then used to digest only the undesired sequences. The remainder of the amplicon strands, because they are single-stranded, are not susceptible to this digestion.

EXAMPLE 10

RDA to Detect Sequences Shared Between Two Populations

In some instances, it is desirable to identify shared transcripts that are expressed in two or more different populations of tester RNA molecules but that are not expressed in a driver RNA population. For example, it would be valuable to identify general cellular response genes that are commonly expressed in multiple samples that are derived in conjunction with conditions such as inflammation or viral infection. If their identity were known, such gene products could provide targets for new pharmaceuticals, or could serve themselves as the basis for new pharmaceuticals. RDA can be adapted to this purpose by applying the scheme outlined in FIGS. 2 and 3, which is called "difference product comparison by subtraction," or DPCS.

The simplest application of DPCS (FIG. 2), employs only two sources of target nucleic acid molecules. Labeled "sample A" and "sample B" in the figure, these could represent RNA from a cell line infected with two different viruses suspected of triggering similar cellular responses. Difference products DP(A) and DP(B) are prepared by using cDNA from each virus-infected cell as a source of tester amplicon DNA, and using cDNA from the uninfected cell lines to prepare driver DNA. The uninfected cells are a "background tissue" in that they contain the majority of the sequences expected to be expressed in both lines of infected cells, i.e., cellular housekeeping gene transcripts, and so on. Thus, this first RDA experiment is employed to reduce the overall complexity of the difference products that will be analyzed in later steps.

Figure 2:
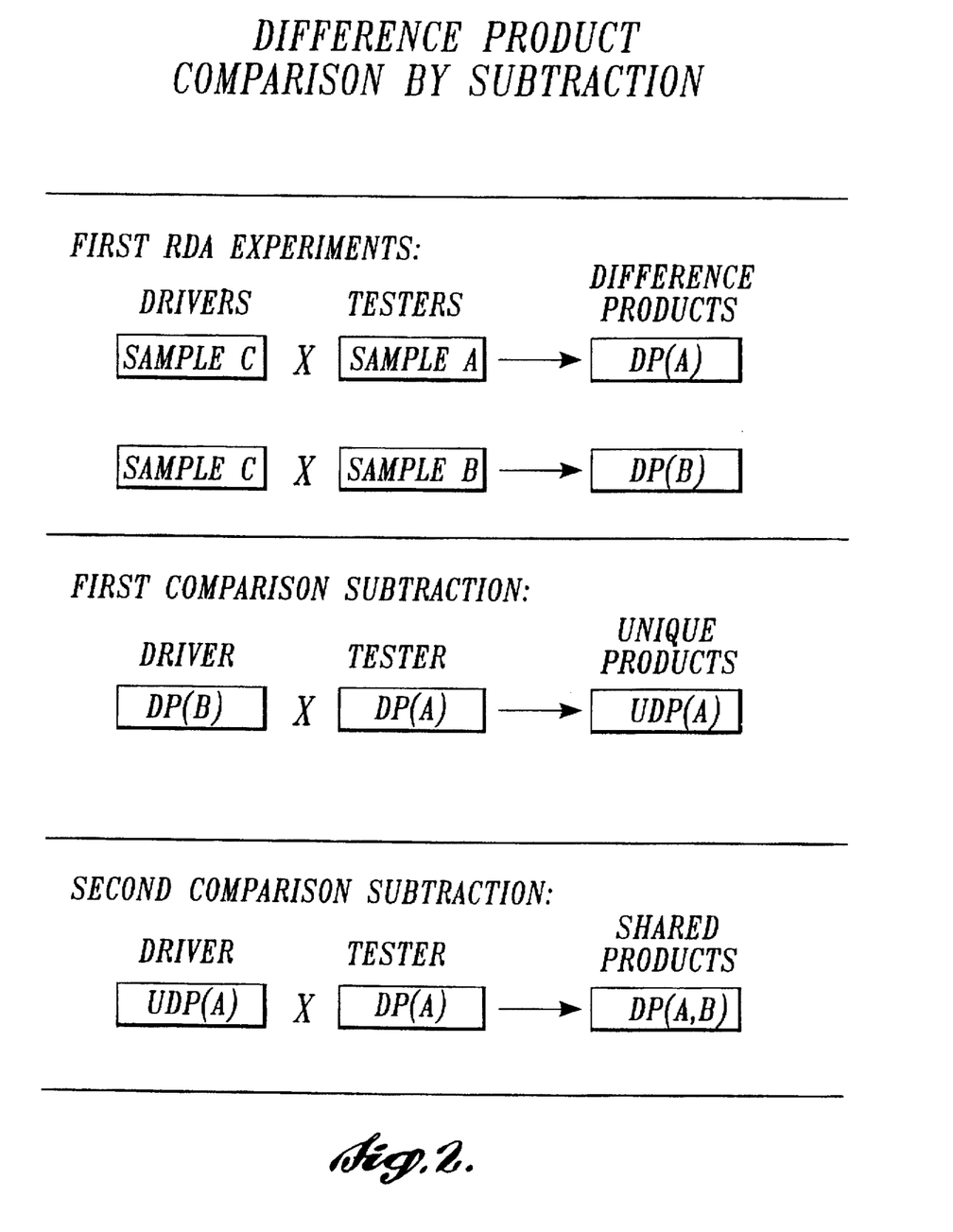
FIGS. 2 and 3 illustrate the use of RDA to identify and isolate those sequences that are shared between two or more RNA populations.

In the first comparison subtraction FIG. 1), DP(B) is used as the driver and DP(A) as the tester to obtain RDA difference products corresponding to those sequences present in DP(A) but absent from DP(B). As these products are unique to DP(A), they are called "UDP(A)." In the subsequent comparison subtraction, UDP(A) is used as the driver and DP(A) as the tester. The resulting difference products represent only the sequences not unique to DP(A), i.e., the sequences shared by DP(A) and DP(B), which are designated in FIG. 1 as DP(A,B).

Figure 3:
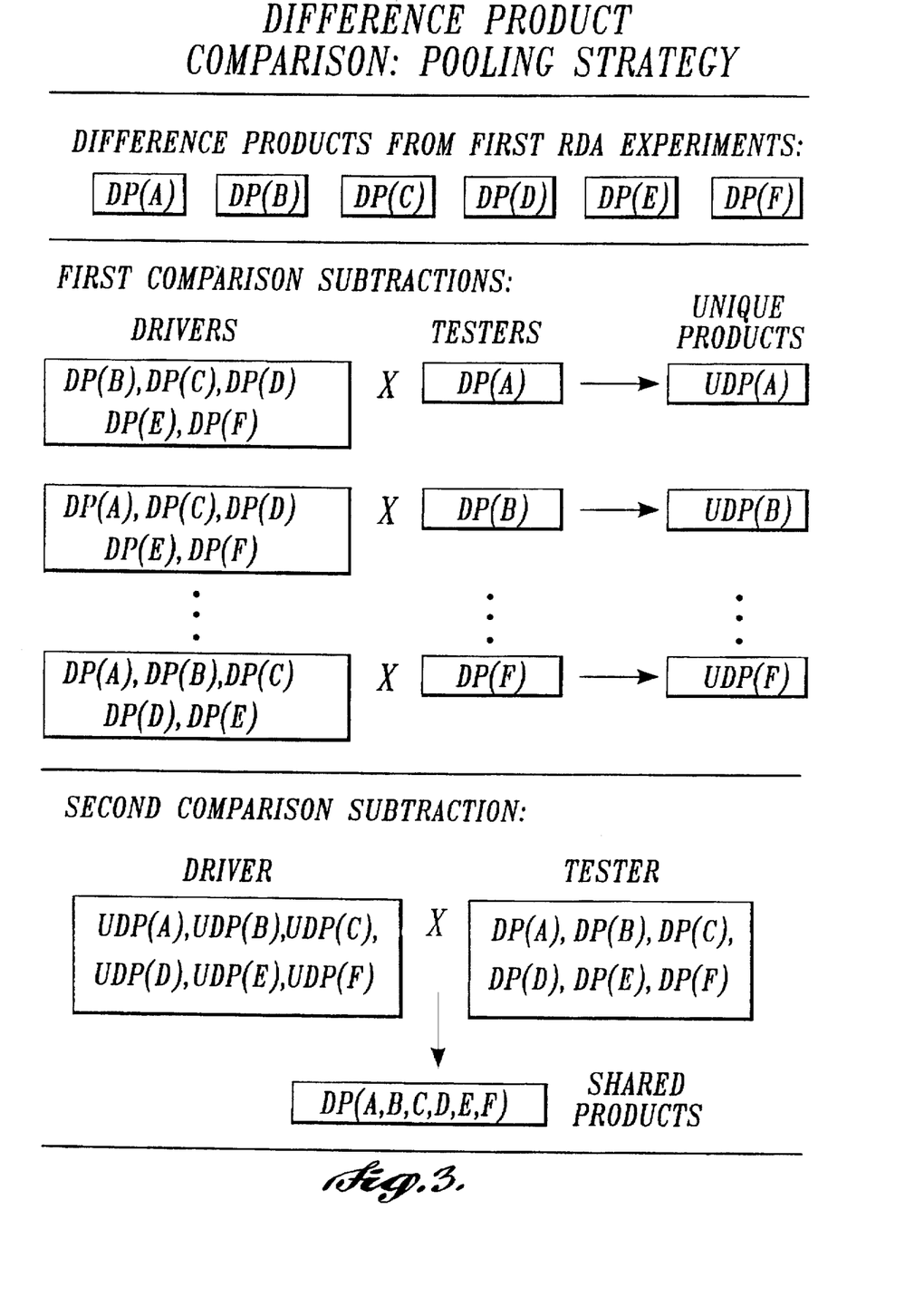

FIG. 3 illustrates how sample pooling can be used to adapt this strategy for isolating sequences shared among more than two nucleic acid populations. The approach is similar, except that during the first comparison subtractions, the drivers are pooled as shown in the figure, and the unique products are pooled as shown for the second comparative subtraction step. It should be apparent that by employing various combinations of difference products as driver or tester, one can design experiments to enrich for sequences shared by any pair or by all of the nucleic acid populations being tested.

Although this example describes primarily the application of this strategy to RNA populations, it can be similarly applied to analyze genes. For example, this scheme can be applied to identify those genes shared by two or more strains of a DNA virus, or to identify unusual genes common to a group of individuals.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for enriching target nucleic acid sequences that are present in a first source of nucleic acid but absent from a second source of nucleic acid, comprising:

preparing amplicon DNA to be used as tester DNA from a first source of nucleic acid comprising the target nucleic acid sequences and preparing amplicon DNA to be used as driver DNA from a second source of nucleic acid that lacks the target nucleic acid sequences;

combining and melting the tester amplicon DNA and the driver amplicon DNA;

reannealing the tester amplicon DNA in the presence of an excess of driver amplicon DNA in an aqueous mixture comprising phenol, wherein the phenol is sustained in emulsion in the aqueous mixture by alternatively heating the mixture to a temperature at which the phenol dissolves but at which the reannealed DNA does not melt, preferably to at least about 65° C., and then cooling the mixture to a temperature at which the phenol becomes substantially insoluble, preferably at or below about 25° C., and whereby at least a portion of the reannealed DNA comprises tester-tester hybrids comprising the target nucleic acid sequences; and selectively amplifying the tester-tester hybrids to obtain enrichment of the target nucleic acid sequences.

2. The method of claim 1, wherein during the reannealing step the driver amplicon DNA is present in at least a 10-fold excess over the tester amplicon DNA.

3. The method of claim 1, wherein from about 1 pg to about 1 ng of tester amplicon DNA is reannealed in the presence of at least about 100 ng of driver amplicon DNA.

4. The method of claim 1, wherein the aqueous mixture comprises from about 11% to about 13% by volume of phenol.

5. The method of claim 1, wherein the first and second sources of nucleic acid are genomic DNA.

6. The method of claim 1, wherein the first and second sources of nucleic acid are cellular RNA.

7. The method of claim 1, wherein the duration of the reannealing step is two hours or less.

8. A method for enriching target nucleic acid sequences that are present in a first source of nucleic acid and also are present in a second source of nucleic acid, comprising:

preparing a first set of RDA difference products between a background tissue and the first source of nucleic acid and a second set of RDA difference products between a background tissue and the second source of nucleic acid, the second source of nucleic acid containing at least one nucleic acid sequence shared with the first source of nucleic acid;

reannealing an excess of the second set of RDA difference products with the first set of RDA difference products whereby at least a portion of the reannealed DNA forms hybrids comprising nucleic acid sequences unique to the first set of difference products;

recovering and selectively amplifying the hybrids comprising nucleic acid sequences unique to the first set of difference products to obtain a third set of difference products;

reannealing an excess of the third set of difference products with the first set of difference products; and selectively amplifying the resulting hybrids, such hybrids having the character of being shared by the first and the second sets of difference products.

* * * * *

UNITED STATES PATENT AND TRADEMARK OFFICE
CERTIFICATE OF CORRECTION

PATENT NO. : 5,759,780
DATED : June 2, 1998
INVENTOR(S) : J.D. Parker et al.

It is certified that error appears in the above-identified patent and that said Letters Patent is hereby corrected as shown below:

Title page, item [56], References Cited:

| COLUMN | LINE | |
|---|---|---|
| 2 | 6 | "Isuchiya" should read --Tsuchiya-- |
| 2 | 10 | "Iechnique" should read --Technique-- |
| 2 | 12 | "techique" should read --technique-- |
| 2 | 14 | "Miller R.D. and Riblet" should read --Miller, R.D. and Riblet, R.-- |
| 2 | 14 | "emilsion" should read --emulsion-- |

Column 6, line 67 after "duplexes." insert a paragraph break
Column 14, line 67 after "MS2" insert a space
Column 21, line 10 before "Fig." insert --(--

Signed and Sealed this

Twenty-ninth Day of September, 1998

Attest:

BRUCE LEHMAN

*Attesting Officer*   *Commissioner of Patents and Trademarks*